United States Patent [19]

Murray et al.

[11] Patent Number: 4,758,507

[45] Date of Patent: Jul. 19, 1988

[54] PRODUCTS DISPLAYING THE ANTIGENICITY OF HEPATITIS B VIRUS E ANTIGENS AND METHODS OF PRODUCING THOSE ANTIGENS

[75] Inventors: Kenneth Murray, Heidelberg, Fed. Rep. of Germany; Patricia MacKay, Cornwall, England

[73] Assignee: Biogen N.P., Curacao, Netherlands Antilles

[21] Appl. No.: 784,115

[22] Filed: Oct. 4, 1985

Related U.S. Application Data

[62] Division of Ser. No. 414,439, Sep. 2, 1982, Pat. No. 4,563,523.

[30] Foreign Application Priority Data

Sep. 2, 1981 [GB] United Kingdom ............... 8126583

[51] Int. Cl.$^4$ .................... C07K 1/00; C07K 3/00; G01N 33/563; G01N 33/576
[52] U.S. Cl. ................................. 435/5; 435/7; 435/68; 435/810; 436/543; 530/403; 530/412; 530/806; 530/810; 530/825; 530/826
[58] Field of Search ................. 435/5, 68, 7, 810; 436/543; 530/403, 412, 806, 810, 825, 826

[56] References Cited

U.S. PATENT DOCUMENTS

| | | | |
|---|---|---|---|
| 3,636,191 | 1/1972 | Blumberg et al. | 424/89 |
| 4,017,360 | 4/1977 | Bertland et al. | 195/14 |
| 4,021,540 | 5/1977 | Pollack et al. | 424/86 |
| 4,102,996 | 7/1978 | McAleer et al. | 424/89 |
| 4,118,479 | 10/1978 | Prince et al. | 424/89 |
| 4,138,287 | 2/1979 | Andersson et al. | 424/89 |
| 4,162,192 | 7/1979 | Mizuno et al. | 424/89 |
| 4,164,565 | 11/1979 | Prince et al. | 424/89 |
| 4,164,566 | 11/1979 | Provost et al. | 424/89 |
| 4,197,361 | 4/1980 | Hoff et al. | 424/8 |
| 4,204,989 | 5/1980 | McAleer et al. | 200/112 B |
| 4,234,564 | 11/1980 | McAleer | 436/820 X |
| 4,301,250 | 11/1981 | Marks et al. | 435/235 |
| 4,617,260 | 10/1986 | McAleer | 436/820 X |

FOREIGN PATENT DOCUMENTS

| | | |
|---|---|---|
| 875596 | 10/1979 | Belgium . |
| 5864 | 12/1979 | European Pat. Off. . |
| 12686 | 12/1979 | European Pat. Off. . |
| 13828 | 8/1980 | European Pat. Off. . |
| 2049515 | 12/1979 | Fed. Rep. of Germany . |
| 2034323 | 6/1980 | United Kingdom . |

OTHER PUBLICATIONS

A. M. Maxam & W. Gilbert, "Sequencing En-Labeled DNA with Base-Specific Chemical Cleavages", *Methods Enzymol.*, 65, pp. 499–560 (1980).

O. Ouchterlony, in *Progress in Allergy*, P. Kallos & R. Waksman (Eds.), Karger, New York, 5, pp. 1–78 (1958).

Maxam, A. M. et al., Proc. Natl. Acad. Sci. USA, 74 (2), 560–564 (1977).

"Handbook of Experimental Immunology", D. M. Weir, Ed., Chapter 19 by O. Ouchterlony, pp. 655–706, Blackwell, Oxford, England, 1967.

V. D. Waart, M. et al., J. Med. Virol., 3(1), 43–49 (1978).

Katz, D. et al., J. Med. Virol., 5(1), 87–100 (1980).

Chemical Abstracts, I, 93:5802t (1980).

Chemical Abstracts, II, 97:160725w (1982).

Chemical Abstrats, III, 102:172627a (1985).

(List continued on next page.)

*Primary Examiner*—Sidney Marantz
*Attorney, Agent, or Firm*—James F. Haley, Jr.; Margaret A. Pierri

[57] ABSTRACT

Polypeptides displaying the antigenicity of hepatitis B virus e antigens, DNA sequences coding for those polypeptides, antibodies to those polypeptides and methods of producing and using those polypeptides, antibodies and DNA sequences. The polypeptides and antibodies of this invention are characterized by their use in compositions and methods for detecting hepatitis B virus infective carriers and in evaluating the course of HBV-related active liver disease.

6 Claims, 3 Drawing Sheets

OTHER PUBLICATIONS

H. Boyer and D. Roulland-Dussoix, "A Complementation Analysis of the Restriction and Modification of DNA in *Escherichia Coli*", *J. Mol. Biol.*, 41, pp. 459-472 (1969).

S. Broome and W. Gilbert, "Immunological Screening Method to Detect Specific Translation Products", *Proc. Natl. Acad. Sci. USA*, 75, pp. 2746-2749 (Jun. 1978).

A. Budkowska et al., "Identification of Two HBeAg Subspecificities Revealed by Chemical Treatment and Enzymatic Digestion of Liver-Derived HBcAg", *J. Immunol.*, 123, pp. 1415-1416 (1979), [Budkowska et al. I].

A. Budkowska et al., "Immunochemistry and Polypeptide Composition of Hepatitis B Core Antigen (HBcAg)", *J. Immunol.*, 118, pp. 1300-1305 (1977), [Budkowska et al. II].

C. J. Burrell et al., "Expression in *Escherichia Coli* of Hepatitis B Virus DNA Sequences Cloned in Plasmid pBR322", *Nature*, 279, pp. 43-47 (May 1979).

P. Charnay et al., "Cloning in *Escherichia Coli* and Physical Structure of Hepatitis B Virion DNA", *Proc. Natl. Acad. Sci. USA*, 76, pp. 2222-2226 (1979).

D. Clewell, "Nature of Col $E_1$ Plasmid Replication in *Escherichia Coli* in the Prsence of Chlorampheicol", *J. Bacteriol*, 110, pp. 667-676 (1972).

B. J. Cohen & Y. E. Cossart, "Application of A Screening Test for Antibody to Hepatitis B Core Antigen", *J. Clin. Path.*, 30, pp. 709-713 (1977).

D. S. Dane et al., "Virus-Like Particles in Serum of Patients with Australian-Antigen-Associated Hepatitis", *The Lancet*, pp. 695-698, (Apr. 4, 1970).

J. Edman et al., "Synthesis of Hepatitis B Surface and Core Antigens in *E. Coli*", *Nature*, 291, pp. 503-506 (1981).

H. A. Fields et al., "Purification and Partial Characterization of Hepatitis e Antigen", *Infection & Immunity*, 20, pp. 792-803 (1978).

A. Fritsch et al., "Cloning of the Genome of Hepatitis B Virus in *Escherichia Coli*", *C. R. Acad. Sc. Paris*, t. 287, Ser. D., pp. 1453-1456. (Dec. 18, 1978)—translation included.

F. Galibert et al., "Nucleotide Sequence of the Hepatis B Virus Genome (Subtype ayw) Cloned in *E Coli*", *Nature*, 281, pp. 646-650 (Oct. 25, 1979).

T. A. Landers et al., "Structure of Hepatitis B Dane Particle DNA and Nature o the Endogenous DNA Polymerase Reaction", *J. Virology*, 23, pp. 368-376. (Aug. 1977).

L. I. Lutwick & W. S. Robinson, "DNA Synthesized in the Hepatitis B Dane Particle DNA Polymerase Reaction", *J. Virology*, 21, pp. 96-104 (Ja. 1977).

P. MacKay et al., "The Conversion of Hepatitis B Core Antigen Synthesized in *E. Coli* into e Antigen", *J. Med. Virol.*, 8, pp. 237-243 (1981).

L. Magnius et al., "A New Antigen–Antibody System", *J. Amer. Med. Assoc.*, 231, pp. 356-359, (1975).

L. Magnius & J. Espmark, "New Specificities in Australia Antigen Positive Sera Distinct from the LeBuvier Determinants", *J. Immunol.*, 109, pp. 1017-1021 (1972).

M. Mandel & A. Higa, "Calcium-Dependent Bacteriophage DNA Infection", *J. Mol. Biol.*, 53, pp. 159-162 (1970).

J. L. Melnick et al., "Approaching the Control of Viral Hepatitis Type B", *J. Infectious Diseases*, 133, pp. 210-225 (1976).

A. R. Neurath et al., *J. Genl Virol.*, 30, pp. 277-285 (1976).

A. R. Neurath & N. Strick, "Host Specificity of a Serum Marker for Hepatitis B: Evidenc that e Antigen has the Properties of an Immunogloublin", *Proc. Natl. Acad. Sci. USA*, 74, pp. 1702-1706 (1977).

H. Ohori et al., "Antigenic Conversion from HBcAg to HBeAg by Degradaton of Hepatitis B Core Particles", *Interviroloyg*, 13, pp. 74-82 (1980).

M. Pasek et al., "Hepatitis B Virus Genes and Their Expression in *E. Coli*", *Nature*, 282, pp. 575-579 (Dec. 6, 1979).

B. G. Werner et al., "Association of e Antigen with Dane Particle DNA in Sera from Asymptomatic Carriers of Hepatitis B Surface Antigen", *Proc. Natl. Acad. Sci. USA*, 74, pp. 2149-2151 (May 1977).

H. Yoshizawa et al., "Demonstration of Hepatitis B e Antigen in Hepatitis B Core Particles Obtained from the Nucleus of Hepatocytes Infected with Hepatitis B Virus," *J. Gen. Virol.*, 42, pp. 513-519 (1979).

W. S. Robinson, "The Genome of Hepatitis B Virus", *Ann. Rev. Microbiol.*, 31, pp. 357-377 (1977).

J. J. Sninsky et al., "Cloning and Endonuclease Mapping of the Hepatitis B Viral Genome", *Nature* 279, pp. 346-348 (May 24, 1979).

(List continued on next page.)

OTHER PUBLICATIONS

S. Stahl et al., "Hepatitis B Virus Core Antigen, Its Synthesis in *Escherichia coli* and Application in Diagnosis", *Proc. Natl. Acad. Sci. USA*, 79, pp. 1606–1610 (1981).

J. Summers et al., "Genome of Hepatitis B Virus: Restriction Enzyme Cleavage and Structure of DNA Extracted from Dane Particles", *Proc. Natl. Acad. Sci. USA*, 72, pp. 4597–4601 (Nov. 1975).

K. Takahashi et al., "Association of Dane Particles with e Antigen in the Serum of Asymptomatic Carriers of Hepatitis B Surface Antigen", *J. Immunol.*, 117, pp. 102–105 (1976).

K. Takahashi et al., "Demonstration of Hepatitis B e Antigen in the Core of Dane Particles", *J. Immunol.*, 122, pp. 275–279 (1979).

K. Takahashi et al., Hepatitis B e Antigen Polypeptides Isolated from Sera of Individuals Infected with Hepatitis B Virus: Comparison with HBeAg Polypeptide Derived from Dane Particles", *J. Gen. Virol., 50, pp. 49–57 (1980) [Chem. Abstracts 94: 63509; (1981)]*.

P. Valenzuela et al. "Nucleotide Sequence of the Gene Coding for the Major Protein of Hepatitis B Virus Surface Antigen", *Nature* 280, pp. 815–819 (Aug. 30, 1979).

G. N. Vyas et al., "Hepatitis B Virus 'e' Antigen: An Apparent Association With Lactate Dehydrogenase Isoenzyme-5", *Science,* 198, pp. 1068–1070 (1977).

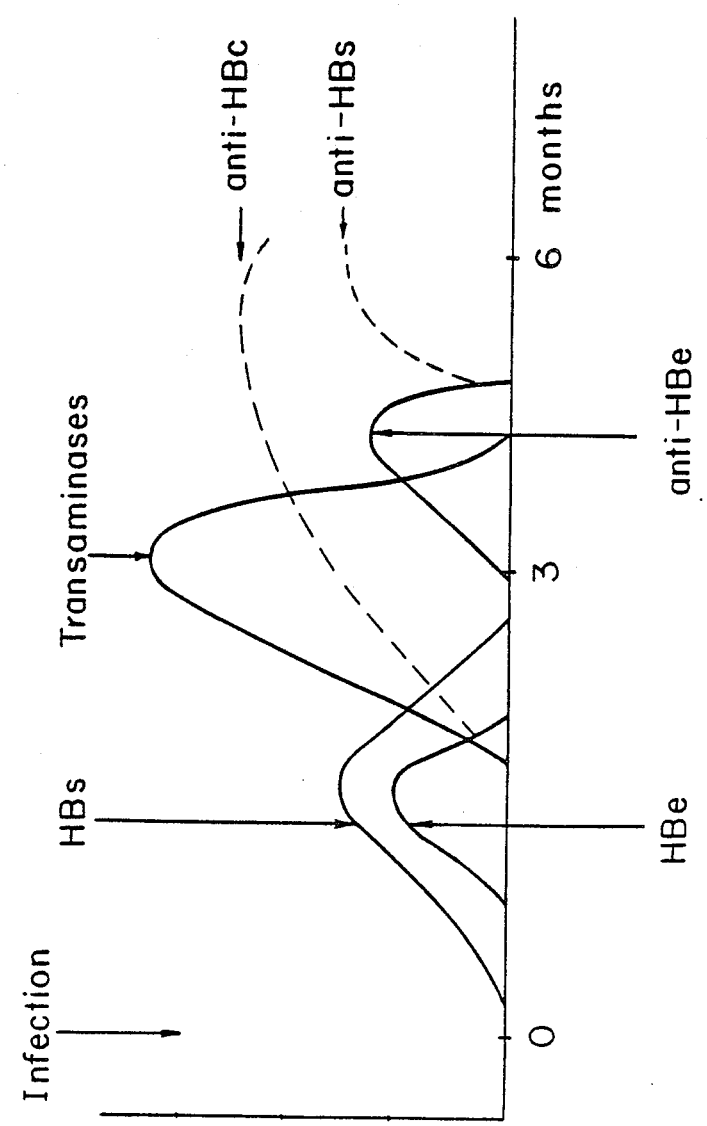

PRODUCTS DISPLAYING THE ANTIGENICITY OF HEPATITIS B VIRUS E ANTIGENS AND METHODS OF PRODUCING THOSE ANTIGENS

This is a division of application Ser. No. 414,439, filed Sept. 2, 1982, now U.S. Pat. No. 4,563,423.

TECHNICAL FIELD OF INVENTION

This invention relates to products displaying the antigenicity of hepatitis B virus e antigens ("HBeAg") and methods for their production. This invention relates more particularly to polypeptides displaying the antigenicity of HBeAg and their production either from polypeptides displaying the antigenicity of hepatitis B virus core antigen ("HBcAg") or from hosts that have been transformed with DNA sequences encoding polypeptides displaying the antigenicity of HBeAg. As will be appreciated from the disclosure to follow, polypeptides displaying the antigenicity of HBeAg may be used in the detection of past or present hepatitis B virus ("HBV") infection, being of particular value in detecting HBV infective carriers and in evaluating the course of HBV-related chronic liver disease.

BACKGROUND ART

Hepatitis B virus (or HBV) infects humans at a very high rate. It is estimated that 15% of the U.S. population have been infected, and in some African and Asian countries, as much as 20% of the adult population are contagious chronic HBV carriers, with over 50% infected.

HBV infection is transmitted by three general mechanisms: (1) by inoculation with infected blood or body fluids, either in large amounts (as in blood transfusions) or in small amounts (as in an accidental skinprick); (2) by close family or sexual contact; and (3) by infection during pregnancy, where the mother transmits the virus to her child.

Most HBV infections are subclinical, and recovery from both subclinical and clinical infections is usually complete. However, serious long term consequences occur in some cases: (1) about 5% of acute HBV infections result in chronic HBV infection, with the constant potential for infectivity to others and for serious, debilitating liver disease, and (2) it is likely that past infection with HBV may be partly or even wholly responsible for the initiation of fulminant hepatitis, cirrhosis, and primary liver cancer. For example, the normal incidence of primary liver cancer is 1:100,000, but for chronic HBV sufferers the incidence of that cancer is 1:300.

The widespread occurrence of HBV, together with its virulence and its association with chronic or lethal liver disease, constitutes a clinical problem of considerable importance. At constant risk are: (1) blood recipients, patients undergoing hemodialysis or renal dialysis, and the institutionalized; (2) their families and (3) all health professionals (particularly nurses, surgeons and dentists). Hence, it is of paramount importance that carriers of infective HBV be easily and accurately identified and treated.

Identification of carriers of HBV infection has been previously difficult, due both to the nature of the virus and its infective course. Infective carriers often show no symptoms of infection and cannot be identified by routine medical examination. Direct assay for live virus is hampered by the facts that the virus is at best only very poorly propagated in cultured cells and that it is not infectious to small laboratory animals. However, it is known that HBV infection causes development of antibodies to proteins (also called antigens) which are part of the virus. Therefore, assays have been developed to detect the presence of these antigens—hepatitis B surface antigen (HBsAg), hepatitis B core antigen (HBcAg), hepatitis B virus e antigen (HBeAg)—or their antibodies.

Unfortunately, the presence of antibodies to HBsAg or HBcAg in the blood may indicate only a past HBV infection and does not necessarily indicate a present potential for HBV infectivity. The third HBV antigen, which may actually be a group of several antigens, hepatitis B virus e antigens, or HBeAgs, (Magnius and Espmark, J. Immunol. 109, pp. 1017–1023 (1972)) may be more useful in such assays. Mounting clinical evidence now suggests: (1) that the presence of HBeAgs in the blood is a definitive marker of contagious HBV infection; (2) that the presence of HBeAgs indicates a particular course of potential HBV-associated liver disease, therefore aiding in prognosis and treatment of that disease; and (3) that the presence of antibodies to HBeAgs signals a favorable prognosis for HBV-associated liver disease.

The problem in using HBeAgs in an assay to pinpoint potential HBV infectivity and to predict the course of liver disease is that it has not been previously possible to produce or to purify useful amounts of HBeAgs or their antibodies in a low cost and efficient manner. As noted above, HBV grows at best very poorly in tissue culture and it does not infect small laboratory mammals. Therefore, conventional means for obtaining these viral antigens are not effective in preparing and isolating sufficient quantities of HBeAgs. Moreover, since such preparations are usually contaminated with large amounts HBcAg, the production of antibodies from them results in a mixture of antibodies to HBcAg and HBeAg. Therefore, such antigen and antibody mixtures are not able to distinguish effectively between HBc- and HBe-containing samples in the various assays and accordingly, such assays are not able to detect unambiguously the presence of HBeAgs. The assays are thus ineffective in detecting infectious carriers of HBV.

Recent advances in recombinant DNA technology have allowed the genes for HBsAg and those for HBcAg to be cloned and their protein products synthesized in bacteria (Burrell et al., Nature 279, pp. 43–47 (1979); Pasek et al., Nature 282, pp. 575–579 (1979); Edman et al., Nature 291, pp. 503–506 (1981)). Therefore, it has been suggested that such technology might provide a means to produce purified hepatitis B virus e antigens, i.e., polypeptides displaying the serological variants of HBeAgs. (see e.g. Edman et al., supra).

Unfortunately, the HBV DNA sequences that code for HBeAgs have not been identified. For example, HBeAg has been variously attributed to the DNA polymerase enzyme of HBV (J. L. Melnick et al., "Approaching The Control Of Viral Hepatitis Type B", J. Infectious Diseases, 133, pp. 210–25 (1976)), an idiotype of IgG (A. R. Neurath and N. Strick, "Host Specificity Of A Serum Marker For Hepatitis B: Evidence That Virus e Antigen Has The Properties Of An Immunoglobulin", Proc. Natl. Acad. Sci. USA, 74, pp. 1702–06 (1977)), a dimer of IgG associated with a small peptide (H. A. Fields et al., "Purification And Partial Characterization Of Hepatitis e Antigen", Infection & Immunity, 20, pp. 792–803 (1978)), associated with lactate dehydrogenase isoenzyme no. 5 (G. N. Vyas et al.

"Hepatitis B Virus e Antigen: An Apparent Association With Lactate Dehydrogenase Isoenzyme 5", *Science*, 198, pp. 1068–70 (1977)), or an antigenic marker on the surface of Dane particles and tubular forms (Neurath et al., *J. Gen. Virol.*, 30, pp. 277–85 (1976)). Accordingly, it has not been previously possible to use recombinant DNA techniques to produce HBeAgs.

It also has been reported that HBeAgs are released from HBV core particles purified from serum (Takahashi et al., *J. Immunol.* 117, pp. 102–105 (1976)) or similar particles purified from liver (Budkowska et al., *J. Immunol.* 123, pp. 1415–1416 (1979); Yoshizawa et al., *J. Gen. Virol.* 42, pp. 513–519 (1979)) by treatment with pronase (Budkowska et al.), pronase and 2-mercaptoethanol (Takahashi et al.), or sodium dodecyl sulphate and 2-mercaptoethanol (Budkowska et al.; Takahashi et al.; Yoshizawa et al.) or by disruption by sonication and by treatment with chaotropic agents or centrifugation in CsCl (H. Ohori et al., "Antigenic Conversion From HBcAg To HBeAg by Degradation Of Hepatitis B Core Particles", *Intervirology*, 13, pp. 74–82 (1980)). However, these methods are not appropriate for the large-scale production of HBeAgs, especially since the resulting products are a mixture of HBc and HBe antigens. Nor do these reports suggest whether HBeAgs are derived from HBcAg or whether HBeAge are different proteins than HBcAg, but which are buried inside the viral particle in such a way that proteolysis of the HBcAg is either necessary for, or an accident to, releasing the HBeAgs. Therefore, these reports do not overcome the difficulty of employing HBeAgs and their antibodies in effective assays or the problems that have prevented the application of recombinant DNA technology to the production of HBeAgs. Moreover, whether HBeAgs are encoded by parts of the HBcAg gene or by entirely separate genes remains unknown. Accordingly, recombinant DNA technology has not been usefully employed to produce HBeAgs.

DISCLOSURE OF INVENTION

The present invention solves the problems referred to by identifying HBcAg as the definitive source of HBeAgs and by providing methods based on the relationship of HBcAg and the HBeAgs—HBcAg may be converted into HBeAg by proteolytic degradation under dissociating conditions—that allow the efficient production of large amounts of HBeAgs and antibodies to those antigens. Alternatively, highly concentrated and substantially pure extracts of HBcAg may be converted to HBeAg in the presence of a reducing agent under dissociating conditions, without proteolytic degradation. Therefore, by virtue of our invention, it is now for the first time possible to obtain HBeAgs and their antibodies in substantial and uncontaminated quantities for use in the identification of HBV infective carriers and as a diagnostic aid in determining the course of HBV-related liver disease and thus in prescribing treatment for that disease.

As will be appreciated from the disclosure to follow, the methods of this invention permit the production of HBeAgs from HBcAg by preparing a bacterial extract of a host characterized by the expression of a polypeptide displaying the antigenicity of hepatitis B virus core antigen and digesting said extract with a reducing agent-resistant protease in the presence of a reducing agent. Alternatively, with more concentrated and purified bacterial extracts, the conversion of HBcAg to HBeAg may be effected by a reducing agent under dissociating conditions. They also permit the production of HBeAgs by the expression in an appropriate host of DNA sequences coding for HBeAgs.

The HBeAgs produced by these processes are useful either as synthesized or after appropriate derivatization or modification in compositions and methods for the detection of antibodies to HBeAgs in human blood serum and for the preparation of antibodies to these HBeAgs for use in the detection of HBeAgs in the blood serum or liver of potentially infective carriers of HBV. HBeAgs themselves or their modifications or derivatives and antibodies produced therefrom may be used separately or together in a HBV diagnostic kits or assays. Moreover, the antigens or their antibodies or both may also be usefully employed in HBV diagnostic kits or in vaccines against hepatitis B virus with one or a combination of any of the following: HBcAg or its modifications or derivatives, antibodies to HBcAg or its modifications or derivatives, HBsAg or its modifications or derivatives, and antibodies to HBsAg or its modifications or derivatives.

BRIEF DESCRIPTION OF THE DRAWINGS

FIG. 3 displays the approximate relationship between the course of HBV infection and the appearance and concentration of the various serological markers of that infection.

BEST MODE OF CARRYING OUT THE INVENTION

Figure 1:
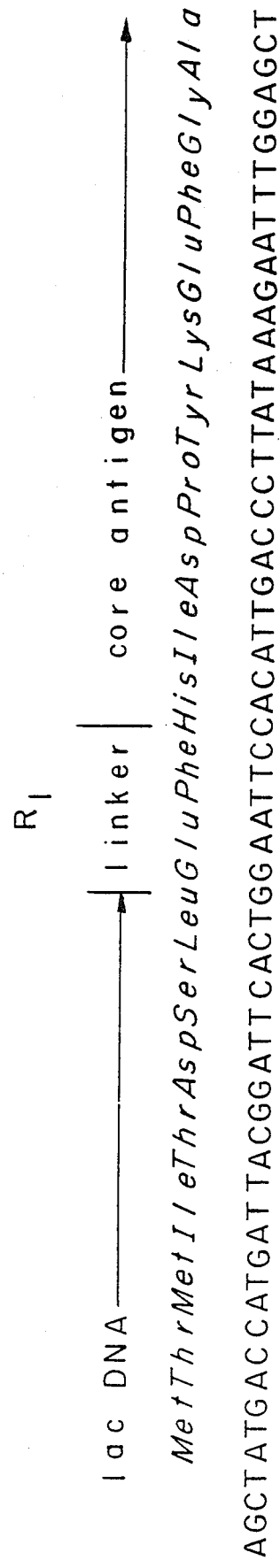
FIG. 1 displays part of the nucleotide sequence of the plasmid pHBV-RI-11. It also displays part of the amino acid sequence of the fusion protein expressed by hosts transformed by plasmid pHBV-RI-11. This protein consists of HBcAg fused to 11 bacterial amino acids. This nucleotide sequence and its protein product are employed in the processes of this invention to enable the production of HBeAg.

In order that the invention herein described may be more fully understood, the following detailed description is set forth.

In the description the following terms are employed:

Polypeptide. A linear series of amino acids connected one to the other by peptide bonds between the α-amino and carboxy groups of adjacent amino acids.

Protein. A polypeptide with approximately 50 or more amino acids.

Antibody. A protein produced by animals in response to the presence of a foreign protein. The antibody binds very strongly and specifically to the foreign protein.

Antigen. Any polypeptide or protein some part or parts of which can be bound by an antibody or antibodies.

Serum. That fraction of blood which remains after red blood cells are removed. It contains, inter alia, antibodies and antigens.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside.

DNA Sequence. A linear series of nucleotides connected one to the other by phosphodiester bonds between the 3' and 5' carbons of adjacent pentoses.

Gene. A DNA sequence which encodes through its template a sequence of amino acids characteristic of a specific polypeptide or protein.

Expression. The process undergone by a gene to produce a polypeptide or protein. It is a combination of transcription and translation.

Expression Control Sequence. A DNA sequence that controls and regulates expression of genes when operatively-linked to those genes.

Cloning Vehicle or Plasmid. A DNA sequence which is able to reproduce itself in a host cell, characterized by one or a small number of endonuclease recognition sites at which such DNA sequences may be cut in a determinable fashion without attendant loss of an essential biological function of the DNA, and which contains a marker, either before or after transformation, suitable for use in the identification of transformed cells, e.g., tetracycline resistance or ampicillin resistance.

Recombinant DNA Molecule. A hybrid DNA sequence comprising at least two nucleotide sequences, the first sequence not normally being found together in nature with the second.

PREPARATION OF REAGENTS

Chemicals. All chemicals and enzymes were purchased from Sigma Chemical Co. with the following exceptions: agarose, from Miles Laboratories, Ltd.; exonuclease BAL 31, from Bethesda Research Laboratories; $\gamma$-$^{32}$P-adenosine triphosphate, from New England Nuclear; polynucleotide kinase, from Boeringer-Mannheim; EcoRI and PstI, from New England Biolabs; EcoRI DNA linkers, from Collaborative Research; and Sephadex G-50, from Pharmacia; and Lyphogel, from Belman Inc. via Hawksley & Son, Lansing, Sussex.

Recombinant Plasmids. Plasmid pHBV-RI-11 which expresses the gene coding for HBcAg when transformed into an appropriate host was constructed as follows. One 1 of a culture of *Escherichia coli* K-12 strain HB101 harboring the plasmid pHBV139A (M. Pasek et al., *Nature* 282, pp. 575-579 (1979)), encoding the entire HBcAg gene on a fragment excisable by PstI, was grown to O.D.$_{550}$=1.0, and the plasmid isolated from the harvested cells as described by D. Clewell, *J. Bacteriol* 110, pp. 667-676 (1972). 60 $\mu$g of purified pHBV139A were digested with 5 units of PstI overnight at 37° C. in 10 mM Tris-HCl (pH 7.6), 5 mM MgCl$_2$, 1 mM dithiothreitol (DTT) and 50 mM NaCl. The digested plasmid was electrophoresed on a preparative 8% polyacrylamide gel and the excised DNA fragment containing the HBcAg coding sequence recovered from the gel by UV-shadowing and elution as described by A. Maxam and W. Gilbert, *Methods Enzymol.* 65, pp. 499-560 (1980). The ends of the isolated DNA fragment were digested with exonuclease BAL 31 in 0.6 ml 20 mM Tris-HCl (pH 8), 12 mM CaCl$_2$, 12 mM MgCl$_2$, 60 mM NaCl and 1 mM ethylenediaminetetraacetic acid (EDTA). The reaction was stopped by extraction with an equal volume of phenol. 0.2 $\mu$g of EcoRI or HindIII linkers (encoding the recognition site of the restriction enzymes EcoRI or HindIII respectively) were phosphorylated by 1 unit of polynucleotide kinase in 10 $\mu$l volume in the presence of adenosine triphosphate (ATP) and $\gamma$-$^{32}$P-ATP in a ratio of 5:1 as described by A. Maxam and W. Gilbert, *Methods Enzymol.* 65, pp. 499-560 (1980).

The phosphorylated and labelled linkers were ligated to 0.2 $\mu$g of the BAL 31-digested fragment with 1 unit of ligase for 1 h at 15° C. in 20 ml of ligation buffer: 50 mM Tris-HCl (pH 7.6), 10 mM MgCl$_2$, 10 mM DTT and 1 mM ATP. The ligation was stopped by phenol extraction as above and the product digested overnight at 37° C. by 10 units of EcoRI or HindIII (as appropriate) and 10 units of BamHI with the addition of 90 $\mu$l of buffer: 10 mM Tris-HCl (pH 7.6), 50 mM NaCl, 5 mM MgCl$_2$, 1 mM DTT and 0.15% Triton X-100. The sample was centrifuged for 1 min in a desktop clinical centrifge through 2 ml of Sephadex G-50 in 10 mM Tris-HCl (pH 8), 1 mM EDTA. 0.2 $\mu$g of pExlac150, a cloning vehicle with an EcoRI or a HindIII restriction site suitable for expressing cloned genes, constructed by H. Weiher, Dissertation, University of Heidelberg (1980) and isolated as described for pHBV139A above, were digested with 1 unit of EcoRI or HindIII and BamHi in 10 $\mu$l of buffer as described above. The above-prepared fragment was then inserted into the cloning vehicle by incubation with 1 unit of ligase in 20 $\mu$l of ligation buffer for 4 h at room temperature.

*Escherichia coli* K-12 strain HB101 (H. Boyer and D. Roulland-Dussoix, *J. Mol. Biol.* 41 pp. 459-72 (1969)) was transformed with the above-prepared recombinant plasmids, as described my M. Mandel and A Higa, *J. Mol. Biol.* 53, pp. 159-162 (1970). Transformants were selected on rich agar plates by resistance to 50 $\mu$g/ml ampicillin and screened for the expression of HBcAg by the method of S. Broome and W. Gilbert, *Proc. Natl. Acad. Sci.* (USA) 75, pp. 2746-2749 (1978), as described by C. Burrell et al., *Nature* 279, pp. 43-48 (1979).

The recombinant plasmid contained by one of the hosts expressing HBcAg, designated pHBV-RI-11 (it contains an Eco RI linker), was sequenced by the method of A. Maxam and W. Gilbert, *Methods Enzymol.* 65, pp. 499-560 (1980) at the region of fusion between the HBV DNA and the $\beta$-galactosidase gene of pExlac150. This nucleotide sequence and corresponding amino acid sequence are displayed in FIG. 1. The nucleotide sequence demonstrates that amino acid 8 of $\beta$-galactosidase is fused to amino acid 3 of HBcAg by 3 amino acids encoded by the EcoRI linker. Other plasmids having various fusions between $\beta$-galactosidase and HBcAg may be similarly isolated.

Antigens. Products displaying the antigenicity of HBcAg were prepared as follows: Two 1 of a culture of *Escherichia coli* K12 strain HB101 harboring the recombinant plasmid pHBV-RI-11 were grown to O.D.$_{550}$=1.0, harvested, and resuspended in 6 ml 50 mM Tris-HCl (pH 8), 25% sucrose. 1 ml 5 mg/ml lysozyme in 0.25 M Tris-HCl (pH 8) was added and the mixture incubated on ice for 5 min. 2.5 ml 0.25 M EDTA were added and the mixture incubated for another 5 min on ice. 10 ml of a solution containing 1% Triton X-100, 0.4% sodium deoxycholate, 50 mM Tris-HCl (pH 8) and 6.25 mM EDTA were added and the mixture again incubated 10 min on ice with occasional shaking. Finally, 1 ml 1 M MgCl$_2$, 0.2 ml 10 mg/ml pancreatic DNase in 0.25 M Tris-HCl (pH 8) were added. The mixture was incubated 1 h at 37° C. and centrifuged in a Sorvall centrifuge with an SS-35 rotor for 10 min at 10,000 rpm. Ammonium sulphate was added (to 55% saturation) and the precipitate collected by centrifugation for 10 min at 10,000 rpm. The precipitate was then redissolved in 10 mM Tris-HCl (pH8) buffer and dialyzed against that buffer. The resulting solution contains bacterially-synthesized polypeptides displaying the antigenicity of HBcAg. It is estimated that these bacterial extracts contain about 1% HBcAg.

Further purification using conventional protein purification techniques permits the preparation of more concentrated solutions of HBcAg, i.e., about 60% pure. The amino acid sequence of the amino-terminus of the HBcAg-related polypeptide of these extracts is displayed in FIG. 1.

Authentic HBcAg was also extracted from autopsy livers of persistent HBcAg carriers as described by B. Cohen and Y. Cossart, *J. Clin. Path.* 30, pp. 709–713 (1977).

Sera. Sera containing antibodies to authentic HBcAg alone and to both authentic HBcAg and authentic HBeAg, as well as serum containing authentic HBeAg, were supplied by the Hepatitis Reference Laboratory at the University of Edinburgh. The sera were concentrated threefold for gel diffusion by treatment with Lyphogel.

Production of Hepatitis B Virus E Antigen

EXAMPLE 1

Figure 2:
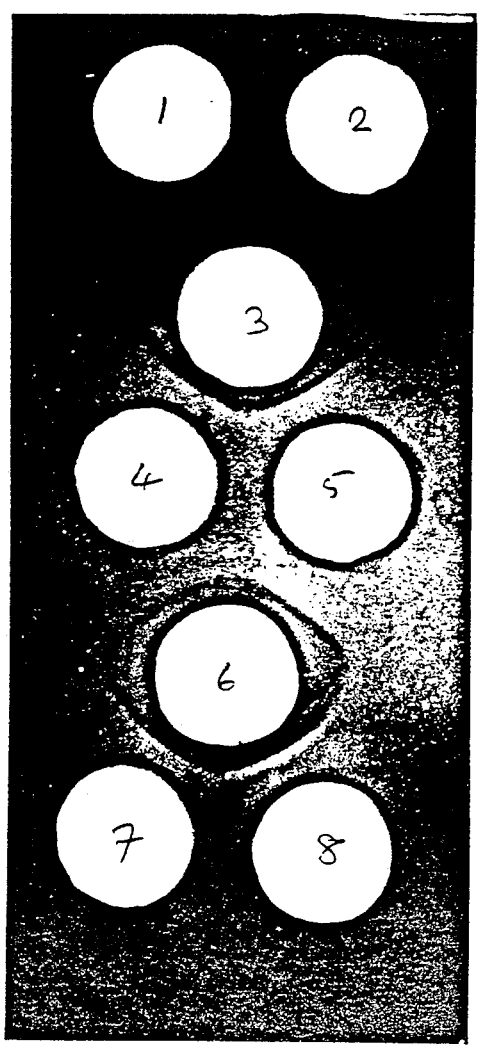
FIG. 2 is a photograph of various immunodiffusion analyses using the HBeAgs produced by one of the processes of this invention.

Aliquots of the supernatant prepared above, i.e., containing bacterially-synthesized polypeptides displaying the antigenicity of HBcAg (about 1% pure), were made 0.1% in pronase or both 0.1% in pronase and 0.1% 2-mercaptoethanol and then incubated for 2 h at 37° C. An aliquot of each sample was tested for the presence of polypeptides displaying the antigenicity of HBcAg or HBeAgs by the immunodiffusion technique of Ouchterlony (O. Ouchterlony, in *Progress in Allergy*, P. Kallos and R. Waksman (Eds.), Karger, New York, Vol. 5, pp. 1–78 (1958)). FIG. 2 is a photograph of a Petri plate containing 0.8% agarose and 0.3% EDTA in 0.1 M barbitone buffer (pH 8.6). It has several wells that are 5 mm in diameter and spaced 2 mm apart. 25 μl of serum, described above, or 25 μl of the supernatant of the bacterial extract, prepared above, were loaded into the wells as follows: human serum positive for anti-HBcAg only (Wells 1, 2, 4 and 5); bacterial extract containing HBcAg without pronase treatment (Well 3); bacterial extract containing HBcAg after treatment with 0.1% pronase in 0.1% 2-mercaptoethanol at 37° C. for 24 h (Well 6); human serum positive for anti-HBcAg and HBeAg (Well 7); and human serum positive for both anti-HBcAg and anti-HBeAg (Well 8). The loaded plates were then incubated at 4° C. for 5 days, washed extensively with 0.1% NaCl and stained for 4 h at room temperature in 0.1% Coomassie Brilliant Blue dye in 45% methanol-5% acetic acid-55% water mixture, and then destained overnight at room temperature in the same solvent. Finally, the dyed plates were photographed.

During the incubation period, the proteins in each sample diffuse through the agarose. Whenever an antigen and its own antibody diffuse past each other, they bind and precipitate and the dye allows visualization of the precipitin line formed by these antigen-antibody complexes. Extracts that had not been digested by the processes of this invention displayed no HBeAg reactivity. However, as FIG. 2 displays, treatment of the bacterial extract with pronase and 2-mercaptoethanol affords an antigenic specificity (a precipitin line between wells 6 and 8) that displays immunological identity with a precipitin line between serum containing HBeAg (well 7) and antibody to HBeAg (well 8), as revealed by the continuity of the line between wells 6, 8 and wells 7, 8.* However, treatment with pronase alone had no effect on the core antigen activity of the bacterial extract. Moreover, treatment of the 1% bacterial extract with SDS alone, SDS plus 2-mercaptoethanol, or 0.5% pronase and 0.1% 2-mercaptoethanol completely destroyed all of the core e or antigenic activity of the extract as measured by immunodiffusion. Similar results were also observed on treatment of the liver extracts.

* With more highly concentrated bacterial extracts (e.g., those containing about 60% HBcAg) the conversion of HBcAg to HBeAg may be effected in the presence of SDS plus 2-mercaptoethanol [Example 2].

Although the above example (with 1% extracts) uses pronase in the present of 2-mercaptoethanol to convert HBcAg into HBeAgs, it should be understood that the conversion of HBcAg into HBeAgs in accordance with that embodiment of the process of this invention can also be accomplished by other reducing agent-resistant proteases (such as subtilisin, papain, chymopapain, bromelin, trypsin, thermolysin, protease K, carboxypeptidase A or carboxypeptidase B) in the presence of other reducing agents (such as dithiothreitol, dithioerythritol, thioglycollate, glutathione and sodium borohydride). Moreover, it should be understood that the relative amounts of such proteases and reducing agents useful in that embodiment of the processes of this invention may be determined by those of skill in the art using the methods and descriptions of this application.

It should also be understood that while the conversion of HBcAg to HBeAg by that embodiment of the processes of this invention appears to involve proteolytic digestion in addition to unfolding and dissociation of HBcAg aggregates, the conversion does not define the extent of such changes. Neither, does the conversion effected by the alternative embodiment (more highly concentrated bacterial extracts, reducing agent, dissociating conditions) of the processes of this invention [Exampale 2]. Therefore, while not wishing to be bound by theory, we believe that the processes of this invention may result in the formation of a population of degradation products, each of which exhibits HBeAg reactivity. These products may represent the various serological variants of HBeAg.

The processes of this invention demonstrate that treatment of HBcAg, derived either from extracts of bacteria or other appropriate hosts harboring a plasmid which expresses the HBcAg gene or from liver of patients with HBcAg in the blood, with a reducing agent-resistant protease, preferably a pronase, and a reducing agent, preferably 2-mercaptoethanol, or alternatively with more highly concentrated starting materials in the presence of a reducing agent and dissociating conditions, converts HBcAg to HBeAgs. It also demonstrates that HBeAgs are derived from HBcAg, rather than existing as a separate protein encoded for by a separate gene, because the DNA fragment harbored by the host expressing HBcAg contains only the HBcAg gene. Thus, a host harboring a plasmid that expresses a gene encoding a polypeptide displaying the antigenicity of HBcAg can be cultured in large quantities and the extract treated by the process described above to produce at low cost and in an efficient manner polypeptides displaying HBeAg antigenicity.

To be useful in the process of this invention, it does not matter whether the polypeptide displaying the antigenicity of HBcAg contains just a portion of HBcAg, all of HBcAg, or some or all of HBcAg fused to another protein, all that is required is that enough of the HBcAg is present so that treatment of the extract by the processes of Example 1 will produce polypeptides displaying HBeAg antigenicity with the important medical benefits of allowing for the rapid and effective identification of HBV infective carriers and prediction of the course of HBV-related liver disease. For example, the first 2 amino acids at the C-terminal end of HBcAg and the first 2 amino acids at the N-terminal end of HBcAg have been removed without affecting the production of HBeAgs from these polypeptides by the processes of this invention.

EXAMPLE 2

Aliquots of the supernatant used in Example 1 were purified using conventional means and methods such that they contained about 60% HBcAg. These aliquots were then made about 1% SDS and 10 mM 2-mercaptoethanol added. After incubation for 2h at 37° C., substantially all of the HBcAg present in the aliquot had been converted to HBeAg.

EXAMPLE 3

It is plain from Examples 1 and 2 that HBeAgs are derived from HBcAg. Thus, the need for conversion of HBcAg to HBeAgs can be avoided by modifying the gene coding for HBcAg to produce DNA sequences coding for HBeAgs. This can be accomplished by eliminating those coding sequences from the HBcAg gene not common to both genes. This can be done, for example, by digesting away non-common terminal nucleotides with exonuclease BAL31. Alternatively, a restriction fragment that includes a sequence coding for a polypeptide displaying the antigenicity of HBeAg could be excised from the HBcAg coding sequence. The newly-isolated HBeAg coding sequences, again really a population of such sequences, corresponding to the serological variants of HBeAg, are then inserted into cloning vehicles and operatively-linked there to an expression control sequence. One method for such insertion, as detailed in Example 1, is to insert the newly-prepared HBeAg genes into the expression plasmid pExlac150. This construction permits the synthesis in an appropriate host of fusion proteins containing a few bacterial amino acids attached to polypeptides displaying HBeAg antigenicity. Thus, a host transformed with pExlac150 containing the newly-prepared HBeAg genes, or with any other plasmid that has been constructed by the process of this invention so as to express the HBeAg genes or portions thereof, can easily be cultured in large quantities to produce directly at low cost and in an efficient manner polypeptides displaying HBeAg antigenicity.

As in Example 1, it does not matter if the polypeptides produced by the process of this invention contain just a portion of HBeAg, all of HBeAg, or some or all of HBeAg fused to another protein, all that is required is that enough of the HBeAg coding sequence is present so that the extract contains a polypeptide displaying HBeAg antigenicity. The HBeAg product can then be used directly for the important medical benefits of allowing for the rapid and convenient identification of HBV infective carriers and the prediction of the course of HBV-related liver disease.

USE OF HBeAgs AND THEIR ANTIBODIES IN DETECTING THE PRESENCE OF HBeAg AND ANTIBODIES TO HBeAg

There are methods and diagnostic kits presently available which are designed to detect the presence of HBcAg, antibodies to HBcAg, HBsAg, antibodies to HBsAg, HBeAg and antibodies to HBeAg. These methods and kits enable the course of the hepatitis infection to be monitored by means of the appearance and disappearance of its various serological markers. For example, as displayed in FIG. 3, the appearance of HBeAg marks the start of the infectious phase of virus and the disappearance of anti-HBe marks the end of that phase.

Polypeptides displaying the antigenicity of HBeAg prepared by the processes of this invention and antibodies raised with them can also be employed in these methods to detect the presence of HBeAg and antibodies to HBeAg. These polypeptides and their antibodies may be packaged in diagonstic kits either alone or in combination with any or all of the other HBV antigens and antibodies. These methods and kits, using polypeptides or antibodies of this invention either alone or in combination with the other HBV antigens or antibodies, will allow the rapid and convenient identification of HBV infective carriers and prediction of the course of HBV-related liver disease.

For example, polypeptides displaying the antigenicity of HBeAg and antibodies produced by the methods of this invention can be used in the immunological diagnostic tests currently available for HBV antigen or antibody detection, that is, the radioimmunoassay or the ELISA (enzyme-linked immunosorbant assay). In each assay, both the polypeptides displaying HBeAg antigenicity and antibodies to these polypeptides are used. The antibodies are produced by injecting laboratory animals with the polypeptides of this invention in a suitable solution, such as Freund's adjuvant, followed by bleeding the animal some six weeks later, removing the red blood cells by centrifugation, and using the resulting serum. Two specific examples are given below.

Radioimmunoassay to detect HBeAg: Antibodies to HBeAgs produced as above are attached to a solid phase, for example, the inside of a test tube. A sample of the patient's serum is added to a tube, together with a known amount of polypeptides displaying the antigenicity of HBeAgs, produced as above and labelled with a radioactive isotope such as radioactive iodine. Any HBeAgs in the patient's serum will compete with the labelled polypeptides displaying the antigenicity of HBeAgs for binding with the HBeAg antibodies. The excess liquid is removed, the test tube washed, and the amount of radioactivity measured. A positive result, i.e., that the patient's serum contains HBeAgs, is indicated by a low radioactive count left in the tube.

ELISA to detect antibody to HBeAg: A microtiter plate is coated with HBeAgs, prepared in accordance with this invention, and to this is added a sample of patient's serum. After a period of incubation permitting interaction of any HBeAg antibodies present in the serum with the HBeAgs, the plate is washed. A preparation of anti-human antibodies, raised in a laboratory animal by injection of Semi-Purified human immunoglobulin and then linked to an enzyme, is added. Incubation allows an antibody-antigen reaction to take place, and the plate is then rewashed. Thereafter, enzyme substrate is added to the microtiter plate and incubated for a period of time to allow the enzyme to work on the substrate, and the adsorbance of the final preparation is measured. A large change in adsorbance indicates a positive result.

The details of the radioimmunoassays and ELISA outlined above demonstrate that the production of polypeptides displaying the antigenicity of HBeAgs by the processes of this invention allow HBeAgs and antibodies to HBeAgs to be detected by the standard techniques already routinely employed in medical facilities and research laboratories for the detection of HBcAg, antibodies to HBcAg, HBsAg, and antibodies to HBsAg. Hence, the availability of a low cost and abundant source of substantially pure polypeptides displaying the antigenicity of HBeAg and their antibodies, made possible by the methods of this invention, will allow blood donor centers and general medical laboratories to detect easily and routinely HBeAgs and antibodies to HBeAgs, and thus permit accurate identification of infective carriers of HBV as well as allowing prediction of the course of HBV-related liver disease.

While we have hereinbefore presented a number of embodiments of this invention, it is apparent that our basic construction can be altered to provide other embodiments which utilize the process of this invention. Therefore, it will be appreciated that the scope of this invention is to be defined by the claims appended hereto rather than the specific embodiments which have been presented hereinbefore by way of example.

We claim:

1. A polypeptide displaying the antigenicity of hepatitis B virus e antigens, said polypeptide being characterized by the absence of hepatitis B virus surface antigen and being produced by a process comprising the steps of:
   (a) preparing a bacterial extract of a host characterized by the expression of a polypeptide displaying the antigenicity of hepatitis B virus core antigen; and
   (b) digesting said extract with a reducing agent resistant protease in the presence of a reducing agent to convert the polypeptide displaying the antigenicity of hepatitis B virus core antigen into a polypeptide displaying the antigenicity of hepatitis B virus e antigens.

2. A polypeptide displaying the antigenicity of hepatitis B virus e antigens, said polypeptide being characterized by the absence of hepatitis B virus surface antigen and being produced by a process comprising the steps of:
   (a) preparing a bacterial extract of a host characterized by the expression of a polypeptide displaying the antigenicity of hepatitis B virus core antigen, said extract comprising about 60% of said hepatitis B virus core antigen; and
   (b) treating said extract with a reducing agent under dissociating conditions to convert the polypeptide displaying the antigenicity of hepatitis B virus core antigen into a polypeptide displaying the antigenicity of hepatitis B virus e antigens.

3. A means for detecting antibodies to hepatitis B virus e antigen in samples of blood serum or in liver tissue characterized by at least one polypeptide of claim 1 or 2.

4. A means for detecting hepatitis B virus e antigens in a sample of blood serum or in liver tissue characterized by an antibody to at least one polypeptide of claim 1 or 2.

5. A hepatitis B virus diagnostic kit comprising the components:
   (a) at least one polypeptide of claim 1 or of claim 2 or
   (b) antibodies to said at least one polypeptide; or
   (c) combinations of (a) and (b).

6. In an immunoassay for detecting hepatitis B virus infection wherein a patient's body fluid or a patient's tissue is immunologically assayed the improvement comprising: contacting a sample of the patient's body fluid or the patient's tissue with at least one polypeptide of claim 1 or of claim 2 or with antibodies to said at least one polypeptide or combinations thereof.

* * * * *